United States Patent [19]
Eckhardt et al.

[11] Patent Number: 5,939,379
[45] Date of Patent: Aug. 17, 1999

[54] TRIAZINE DERIVATIVES AND THEIR USE

[75] Inventors: Claude Eckhardt, Riedisheim, France; Dieter Reinehr, Kandern, Germany; Georges Metzger, Moernach, France; Hanspeter Sauter, Schopfheim, Germany

[73] Assignee: Ciba Specialty Chemicals Corporation, Tarrytown, N.Y.

[21] Appl. No.: 08/867,110

[22] Filed: Jun. 2, 1997

[30] Foreign Application Priority Data

Aug. 17, 1996 [GB] United Kingdom ............... 9617322

[51] Int. Cl.⁶ .................... C11D 3/34; C11D 3/395; C11D 3/42; C11D 7/54
[52] U.S. Cl. .................... 510/516; 510/375; 510/461; 544/193.2; 252/186.38
[58] Field of Search .................... 510/367, 375, 510/461, 516; 544/193.2; 252/186.38

[56] References Cited

U.S. PATENT DOCUMENTS 5,744,599  4/1998  Reinehr et al. .................... 544/193.1

FOREIGN PATENT DOCUMENTS

| 0509787 | 10/1992 | European Pat. Off. . |
| 0693483 | 1/1996 | European Pat. Off. . |
| 0728749 | 8/1996 | European Pat. Off. . |
| 814579 | 10/1959 | United Kingdom . |
| 1238833 | 7/1971 | United Kingdom . |
| 2158454 | 11/1985 | United Kingdom . |
| 2291644 | 1/1996 | United Kingdom . |
| 2298422 | 9/1996 | United Kingdom . |
| 9404515 | 3/1994 | WIPO . |
| 9602625 | 2/1996 | WIPO . |

OTHER PUBLICATIONS

Chem. Abst. vol. 55, No. 15, 14921i.
Chem. Abst. 75: 7434
Chem. Abst. 115: 243903
Chem. Abst. 71: 71380
Chem. Abst. 75:49143
H. Hausermann and R. Keller (J.R. Geigy AG, Basel, Switzerland), The Relationships between the Constitution and Accumulation of Optical Brighteners in Washing Processes with Anionic and Nonionic Detergents, Textil Rundschau, pp. 176–180 (1961) and English.

Primary Examiner—Paul Lieberman
Assistant Examiner—John M. Petruncio
Attorney, Agent, or Firm—Kevin T. Mansfield

[57] ABSTRACT

The present invention relates to new compounds which are useful as ultraviolet absorbing agents (UVAs) and as fluorescent whitening agents (FWAs), and to a method of improving the sun protection factor (SPF) of textile fibre material, especially cotton, polyamide and wool, treated with the new compounds.

13 Claims, No Drawings

TRIAZINE DERIVATIVES AND THEIR USE

The present invention relates to new compounds which are useful as ultraviolet absorbing agents (UVAs) and as fluorescent whitening agents (FWAs), and to a method of improving the sun protection factor (SPF) of textile fibre material, especially cotton, polyamide and wool, treated with the new compounds.

It is known that light radiation of wavelengths 280–400 nm permits tanning of the epidermis. Also known is that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, even skin beneath clothing dyed in some dark shades may also require protection from UV radiation.

Such lightweight summer clothing normally has a density of less than 200 g m$^2$ and has a sun protection factor rating between 1.5 and 20, depending on the type of fibre from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, SPF ratings of at least 20 are desired for lightweight clothing.

It is already known, e.g. from WO94/4515, that the application of specified types of UVA to a light-weight textile materials in general can effect an increase in the SPF value of the textile so treated. The increase in SPF value achieved thereby, however, is relatively modest.

The use of FWAs in order to effect an increase in the SPF value of textiles has also been proposed. Most FWAs, however, are only effective in absorbing radiation in the UV-A range.

Certain new compounds have now been found which can be readily produced and which, unexpectedly, absorb radiation in both the UV-A and UV-B ranges, and impart greatly increased SPF ratings to textile fibre materials treated with the new compounds.

Accordingly, the present invention provides, as a first aspect, a compound having the formula:

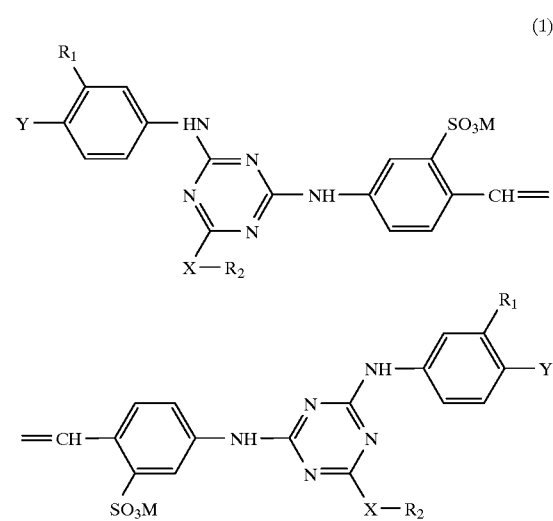

in which M is hydrogen, an alkali metal atom, ammonium or a cation formed from an amine; $R_1$ is hydrogen or hydroxy; $R_2$ is $C_1$–$C_4$alkyl or phenyl; Y is —C(=O)—NR$_3$R$_4$ in which $R_3$ and $R_4$, independently, are hydrogen or $C_1$–$C_4$alkyl, —SO$_2$—NR$_3$R$_4$ in which $R_3$ and $R_4$ have their previous significance, —C(=O)—R$_2$ in which R$_2$ has its previous significance or —C(=O)—OM in which M has its previous significance; and X is NH or O, or X—R$_2$ denotes a morpholino group; provided that those compounds are excluded in which:

a) Y is —C(=O)—OM in which M has its previous significance; X is NH; and R$_2$ is phenyl;
b) R$_1$ is hydrogen; Y is —C(=O)—CH$_3$; and X-R$_2$ denotes a morpholino group; or
c) R$_1$ is hydrogen; Y is —C(=O)—OM in which M has its previous significance; X is NH; and R$_2$ is methyl.

When one or more of $R_2$, $R_3$ and $R_4$ is $C_{1-C4}$alkyl, this group may be branched or unbranched such as methyl, ethyl, propyl, isopropyl, butyl, isobutyl, sec.-butyl or tert.-butyl, especially methyl.

In each of the compounds of formula (1) it is preferred that they are used in neutral form, i.e. that M is other than hydrogen, preferably a cation formed from an alkali metal, in particular sodium, or from an amine.

In the compounds of formula (1), preferably $R_1$ is hydrogen, X—$R_2$ is —NH—$CH_3$ and Y is C(=O)—$NHCH_3$.

The compounds of formula (1) may be produced by reacting, under known reaction conditions, cyanuric chloride, successively, in any desired sequence, with each of an aminostilbene-sulfonic acid, an amino compound capable of introducing a group

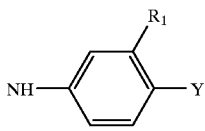

in which $R_1$ and Y have their previous significance, and a compound capable of introducing a group X—$R_2$, in which X and $R_2$ each have their previous significance.

The starting materials are known compounds which are readily available.

The present invention also provides, as a second aspect, a method for the improvement of the SPF of a textile fibre material, comprising treating the textile fibre material with 0.05 to 3.0% by weight, based on the weight of the textile fibre material, of one or more compounds having the formula (1).

The textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m² and have not been previously dyed in deep shades.

Some of the compounds of formula (1) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1) there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$–$C_6$alkanols, the addition products having been converted into an acid ester with an organic dicarboxylic acid or with an inorganic polybasic acid;

lignin sulphonates; and, in particular formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the compound of formula (1) in a concentration such that the desired SPF improvement is achieved.

In certain cases, the compound of formula (1) is made fully effective by an after-treatment. This may comprise a chemical treatment such as treatment with an acid, a thermal treatment or a combined thermal chemical treatment.

It is often advantageous to use the compound of formula (1) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1), a minor proportion of one or more adjuvants may also be employed in the method of the present invention. Examples of adjuvants include emulsifiers, perfumes, colouring dyes, opacifiers, further fluorescent whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1%, and preferably ranges from 0.01 to 1% by weight on the treated fibre.

The method of the present invention, in addition to providing protection to the skin, also increases the useful life of an optionally dyed textile article treated according to the present invention. In particular, the tear resistance and/or lightfastness of the treated textile fibre material may be improved.

The present invention also provides a textile fabric produced from a fibre treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The treatment method according to the present invention may also be conducted by washing the textile fibre material with a detergent containing at least one compound of formula (1), thereby imparting an excellent sun protection factor to the fibre material so washed.

The detergent treatment according to the present invention is preferably effected by washing the textile fibre material at least once with the detergent composition at a temperature ranging from 10 to 100° C., especially from 15 to 60° C.

The detergent composition used preferably comprises:
  i) 5–90%, preferably 5–70% of an anionic surfactant and/or a nonionic surfactant;
  ii) 5–70%, preferably 5–40% of a builder;
  iii) 0–30%, preferably 1–12% of a peroxide;
  iv) 0–10%, preferably 1–6% of a peroxide activator and/or 0–1%, preferably 0.1–0.3% of a bleaching catalyst and/or preferably 0.001–0.05% of a photobleaching agent;
  v) 0.005–2%, preferably 0.01–1% of at least one compound of formula (1); and
  vi) 0.005–10%, preferably 0.1–5% of of one or more auxiliaries, each by weight, based on the total weight of the detergent.

The said detergent compositions are also new and, as such form a further aspect of the present invention.

The detergent may be formulated as a solid, as an aqueous liquid comprising 5–50, preferably 10–35% water or as a non-aqueous liquid detergent, containing not more than 5, preferably 0–1 wt. % of water, and based on a suspension of a builder in a non-ionic surfactant, as described, e.g., in GB-A-2158454.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO(R$^1$)CH$_2$COOM$^1$ in which R is alkyl or alkenyl having 9–17 carbon atoms in the alkyl or alkenyl radical, R$^1$ is C$_{1-C4}$ alkyl and M$^1$ is alkali metal.

The nonionic surfactant component may be, e.g., a condensate of ethylene oxide with a C$_{9-C15}$ primary alcohol having 3–8 moles of ethylene per mole.

The builder component may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula NaHSi$_m$O$_{2m+1}$·pH2O or Na$_2$Si$_m$O$_{2m+1}$·pH$_2$O in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

Any peroxide component may be any organic or inorganic peroxide compound, described in the literature or available on the market, which bleaches textiles at conventional washing temperatures, e.g. temperatures in the range of from 5° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. The peroxides, especially the inorganic peroxides, are preferably activated by the inclusion of an activator such as tetraacetyl ethylenediamine or nonoyloxybenzene sulfonate. Bleaching catalysts which may be added include, e.g., enzymatic peroxide precursors and/or metal complexes. Preferred metal complexes are manganese or iron complexes such as manganese or iron phthalocyanines or the complexes described in EP-A-0509787.

Preferred photobleaching agents are phthalocyanines containing water-solubilising groups such as sulfo groups. As water-soluble phthalocyanines, it is possible to use metal-free phthalocyanines or metal complexes of phthalocyanines. Metal complexes of phthalocyanines are preferably those of aluminium, zinc, magnesium, calcium, iron, sodium or potassium. Particularly preferred photobleaching agents are sulfonated zinc or aluminium phthalocyanines. Mixtures of photobleaching agents may be used such as mixtures of water-soluble zinc and aluminium phthalocyanines.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases and proteases; photobleaching agents; pigments; shading agents; and/or one or more futher fluorescent whitening agents, such as those of the 4,4'-bis-(triazinylamino)-stilbene-2,2'-disulfonic acid, 4,4'-bis-(triazol-2-yl)- stilbene-2,2'-disulfonic acid, 4,4'-(diphenyl) -stilbene, 4,4'-distyryl-biphenyl, 4-phenyl-4'-benzoxazolyl-stilbene, stilbene-naphthotriazole, 4-styryl-stilbene, bis-(benzoxazol-2-yl), bis-(benzimidazol-2-yl), coumarine, pyrazoline, naphthalimide, triazinyl-pyrene, 2-styryl-benzoxazole, 2-styryl-naphthoxazole or benzimidazole-benzofuran types. These auxiliary constituents should, of course, be stable to any bleaching system employed.

Compounds of the formula (I) have also been found to be useful for the fluorescent whitening of textile materials, in which connection polyamides, wool and cotton should be singled out particularly, and of paper.

The compounds of formula (1) are suitable for use in textile detergent or softener compositions which dispense with the use of a fluorescent whitening agent in order to maximise the colour care performance of the compositions.

Certain of the compounds of formula (1), in particular those containing a group Y which has the formula —C(=O)—R$_2$ in which R$_2$ has its previous significance, while improving the sun protection factor of textiles treated with them, are non-fluorescent. Such non-fluorescent compounds of formula (1) are especially suitable for use in textile detergent or softener compositions which dispense with the use of a fluorescent whitening agent in order to maximise the colour care performance of the compositions. Such textile detergent or softener compositions comprising a non-fluorescent compound of formula (1) form a further aspect of the present invention.

The following Examples further illustrate the present invention.

EXAMPLE 1(A)

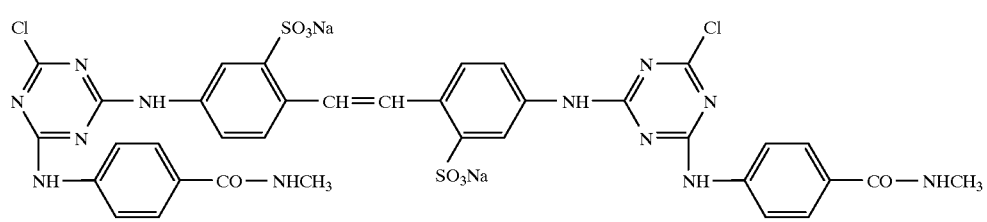

(101)

27.7 g of cyanuric chloride are incorporated into 154 g of acetone and 205 g of ice, cooled to −5° C. and treated, dropwise, with a solution of 27 g of the disodium salt of 4,4'-diaminostilbene 2,2'-disulfonic acid in 190 mls of water. The pH of the reaction mixture is held at 5.5–6.0 by the addition of an aqueous soda solution. The reaction mixture is then treated with a suspension of 22.5 g of 4-aminobenzoylmethylamide in 112 g of acetone. The pH of the reaction mixture is held at 8.0 by the addition of an aqueous soda solution. The resulting suspension is stirred for 27 hours whereupon the temperature rises to 25° C. The precipitate which forms is filtered off, washed and dried in vacuum. In this way, there are obtained 71.7 g of the yellowish compound of formula (101).

Elemental analysis of the compound having the formula (101) and having the empirical formula $C_{36}H_{28}Cl_2N_{12}O_8S_2.8.76$ $H_2O$ gives: Req. % C39.17; H 4.19; N 15.34; S 5.85; Cl 6.17; $H_2O$ 14.41. Found % C 37.7; H4.1; N14.6; S5.6; Cl5.8; $H_2O$ 14.41.

EXAMPLE 1(B)

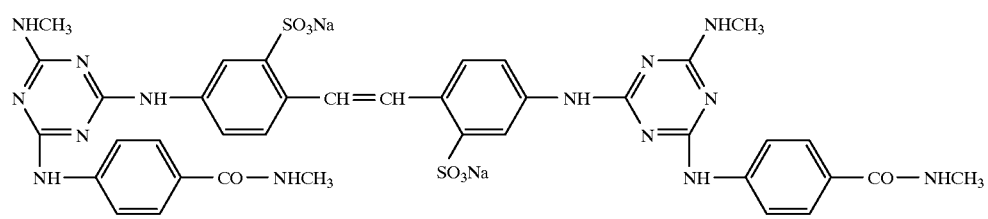

(102)

37.5 g of the compound (101) obtained in Example 1 (A) are dispersed in 500 mls of water and treated with 29 g of an aqueous 40% methylamine solution. The mixture so obtained is slowly heated to 90° C. and stirred at this temperature for 4 hours. The reaction mixture is then treated with 55 g of sodium chloride, cooled to 20° C., filtered and washed. There are obtained 34.1 g of a yellowish compound of formula (102).

Elemental analysis of the compound having the formula (102) and having the empirical formula $C_{38}H_{36}N_{14}Na_2O_8S_2.8.87$ $H_2O$ gives: Req. % C42.00; H4.98; N18.04; S5.90; O 24.84; $H_2O$ 14.70. Found % C 40.9; H 4.9; N 17.5; S 5.6; 0 27.6; $H_2O$ 14.7.

EXAMPLE 2

The compound (102) is produced using the procedure described in Example 1(A) and (B) except that the intermediate compound (101) is not isolated. Using this modified process, 69.5 g of the yellow compound (102) are obtained.

EXAMPLE 3

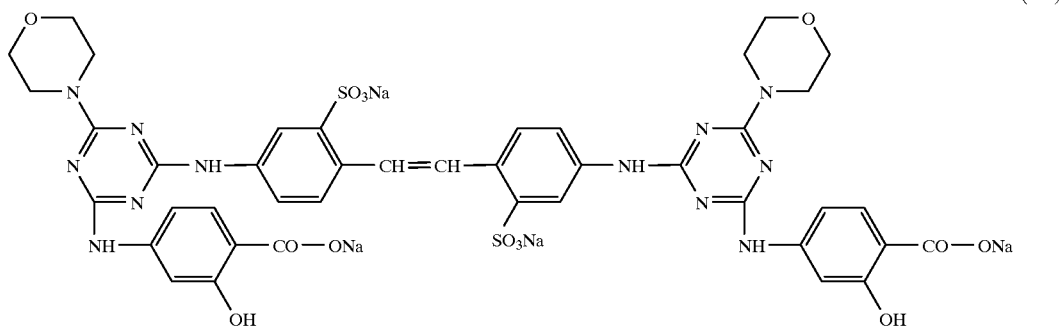

(103)

12.6 g of cyanuric chloride are dissolved in 80 mls of acetone and poured on to 75 g of ground ice. While the mixture so obtained is vigourously stirred and cooled with ice, there is added to the mixture, dropwise, an aqueous solution of 15.6 g of the disodium salt of 4,4'-diaminostilbene-2,2'-disulfonic acid. The addition is conducted over 40–50 minutes and the temperature is not allowed to exceed +5° C. The reaction mixture has a pH of 1. The pH of the reaction mixture is adjusted to 6–7 and the mixture is stirred for 1 hour at 0° C.

There are then added to the reaction mixture 14.53 g of the sodium salt of 4-aminosalicylic acid, followed by the dropwise addition of 34.4 mls of 1M sodium carbonate solution, whereupon the pH of the mixture rises to 10–11. The reaction mixture is heated to 40–50° C. and, after 30 minutes, a clear solution having a pH of 7–8 is obtained. 6 mls of morpholine are added, dropwise, to the reaction mixture. The reaction mixture is distilled and, after the removal of 100 mls of acetone, a clear solution remains. The solid compound (103) is precipitated by the addition of 150 mls of aqueous sodium acetate, separated by suction and re-washed with sodium acetate solution. The moist residue is then boiled with 1 liter of alcohol in order to free it from sodium acetate. After drying, 28.6 g of compound (103) (74% of theory) are obtained.

Elemental analysis of the compound having the formula (103) and having the empirical formula $C_{42}H_{36}N_{12}O_{14}S_2Na_4 \cdot 10.5\ H_2O$ gives: Req. % C 39.49; H 4.49; N 13.15; S 5.01; $H_2O$ 15.09. Found % C 39.46; H 4.53; N 13.26; S 4.89; $H_2O$ 14.78.

EXAMPLE 4

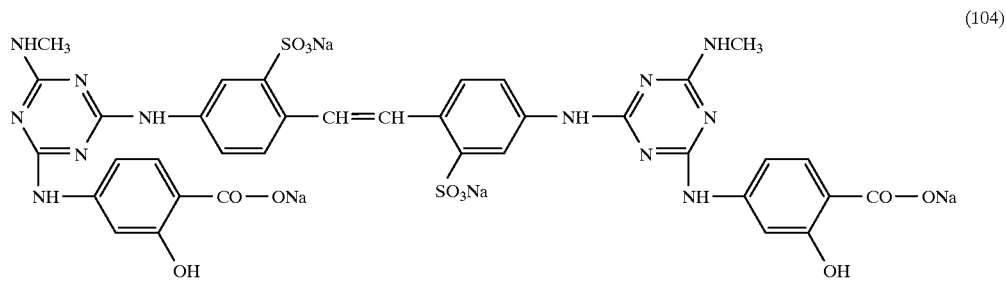

(104)

Using the procedure described in Example 3, but replacing the morpholine reactant used therein by the equivalent amount of methylamine, the compound (104) is obtained in a yield of 98% of theory.

Elemental analysis of the compound having the formula (104) and having the empirical formula $C_{36}H_{28}N_{12}O_{12}S_2Na_4 \cdot 12\ H_2O$ gives: Req. % C 36.25; H 4.34; N 14.09; S 5.37; $H_2O$ 18.1. Found % C 36.16; H 4.41; N 13.85; S 5.30; $H_2O$ 18.5.

EXAMPLE 5(A)

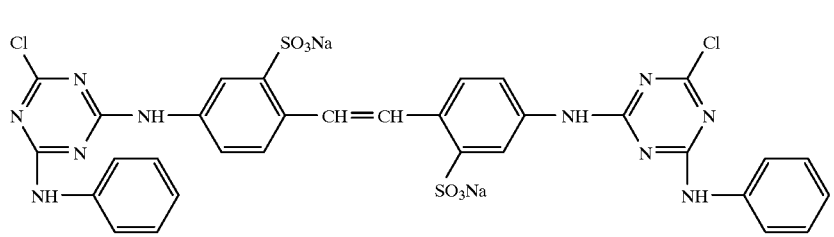
(105)

Using the procedure described in Example 1(A), but replacing the 4-aminobenzoylmethylamide reactant used therein by the equivalent amount of aniline, the compound (105) is obtained.

EXAMPLE 5(B)

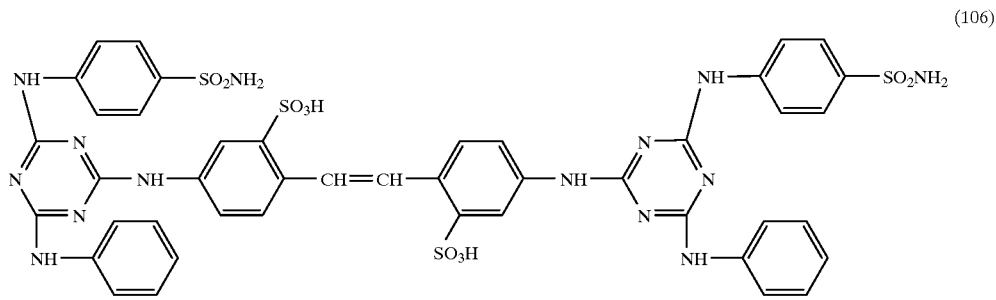
(106)

0.0115 mol of compound (105) is heated to 130° C. in 50 mls of ethyleneglycol monomethylether together with 0.026 mol of sulfanilamide. At first, a clear solution is obtained and then the compound (106) is precipitated as yellow flakes. After filtration by suction and washing with water, 0.009 mol (79.5% theory) of the compound (106) is obtained as a yellow powder.

Elemental analysis of the compound having the formula (106) and having the empirical formula $C_{44}H_{38}N_{14}S_4O_{10} \cdot 3 H_2O$ gives: Req. % C 47.0; H 4.05; N 17.0; S 11.54; $H_2O$ 4.83. Found % C 47.9; H 4.09; N 17.4; S 11.0; $H_2O$ 4.83.

The corresponding sodium salt of compound (106) is obtained by treating the compound (106) with sodium methylate in methanol.

EXAMPLE 6

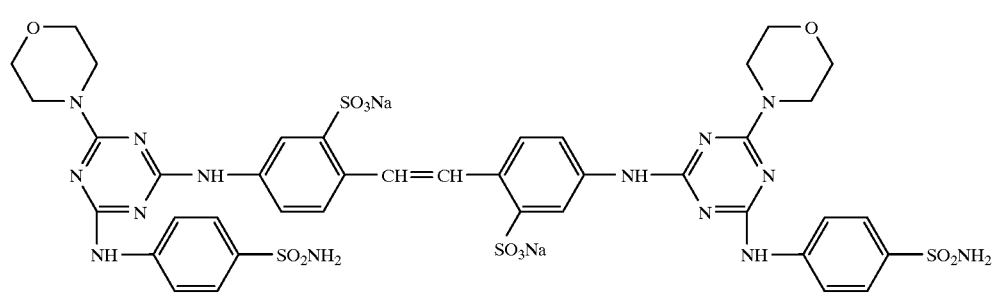
(107)

Using the procedure described in Example 3, but replacing the 4-aminosalicylic acid reactant used therein by sulfanilamide, compound (107) is obtained. The reaction product is isolated by precipitation with sodium chloride. After washing with ice water and drying, 36.28 g (95.4% theory) of compound (107) are obtained.

Elemental analysis of the compound having the formula (107) and having the empirical formula $C_{40}H_{42}N_{14}S_4O_{12}Na_2 \cdot 8\ H_2O$ gives: Req. % C 39.02; H 4.76; N 15.93; S 10.42; $H_2O$ 12.69. Found % C 39.1; H 4.7; N 15.8; S 10.1; $H_2O$ 12.69.

EXAMPLE 7

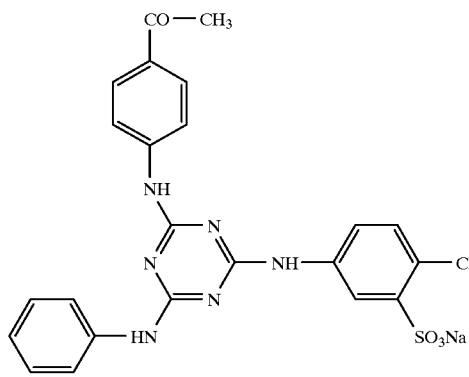
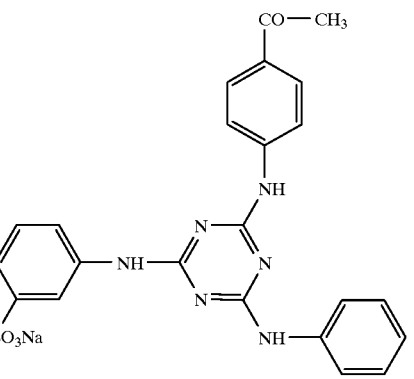

(108)

1.2 g of 4-aminoacetophenone are dissolved in 30 ml of methylcellosolve. To this solution are then added 3.3 g of the compound (91% purity) having the formula:

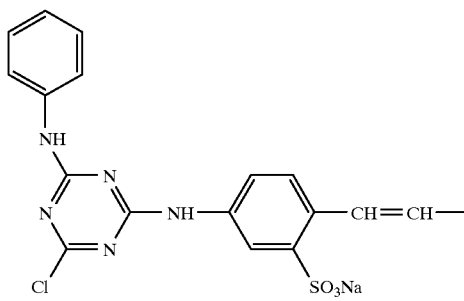
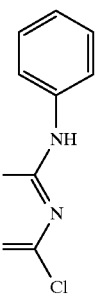

The reaction mixture is heated to 130° C. in an oilbath and held at this temperature for 4 hours. After a short time, the free acid version of the salt compound (108) crystallises out. After filtration with suction, the filtercake, dissolved in methanol, is converted into the disoduim salt of formula (108) using sodium methylate. After filtration with suction, washing with water and drying, there are obtained 4.0 g (91% theory) of the di-sodium salt of formula (108).

Elemental analysis of the compound having the formula (108) and having the empirical formula $C_{48}H_{38}N_{12}Na_2O_8S_2 \cdot 11.0\ H_2O$ gives: Req. % C 47.29; H 4.96; N 13.78; S 5.26; $H_2O$ 16.24. Found % C 47.05; H 4.96; N 13.87; S 5.28; $H_2O$ 15.99.

EXAMPLES 8 to 12

A standard (ECE) washing powder is made up from the following components in the indicated proportions (weight %):

8.0% Sodium ($C_{11.5}$)alkylbenzene sulfonate
2.9% Tallow alcohol-tetradecane-ethylene glycol ether (14 mols EO)
3.5% Sodium soap
43.8% Sodium tripolyphosphate
7.5% Sodium silicate
1.9% Magnesium silicate
1.2% Carboxymethyl cellulose
0.2% EDTA
21.2% Sodium sulfate
0 or 0.19% compound (102) and Water to 100%.

A wash liquor is prepared by dissolving 0.8 g. of the above washing powder in 200 mls. of tap water. 10 g. of bleached cotton fabric is added to the bath and washed at 40° C. over 15 minutes and then rinsed, spin-dried and ironed at 1 60° C. This washing procedure is repeated up to ten times.

After the ten washes, the whiteness and Sun Protection Factor of the washed samples are measured. The whiteness (W) is determined using a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The whiteness is equal to 60 when washed without compound (102) and is 222 when washed with 0.19% of compound (102), on weight of detergent.

The Sun Protection Factor (SPF) is determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

Five measurements are made at different points on each swatch. The average of these 5 measurements is calculated and provides the following results:

SPF is 3 for the initial bleached cotton fabric;

SPF is 4 after 10 washes in the absence of compound (102); and

SPF is 24 after 10 washes with 0.19% of compound (102), on weight of detergent.

When the above procedure is repeated but replacing compound (102) by Compound (103), (104), (106) or (107), the results obtained in the following Table 1 are obtained.

TABLE 1

| Example | Test Compound | W | SPF |
|---------|--------------|-----|-----|
| 9 | (103) | 208 | 21 |
| 10 | (104) | 214 | 19 |
| 11 | (106) | 203 | 18 |
| 12 | (107) | 209 | 17 |

EXAMPLE 13

A series of cotton poplin swatches is dyed using a range of reactive dyes, employing the exhaustion method and the dyeing conditions recommended in the technical bulletin issued for each of the separate reactive dyes.

Each of the swatches is then washed under the following conditions:

A standard (ECE) washing powder is made up from the following components in the indicated proportions (weight %):

8.0% Sodium ($C_{11.5}$)alkylbenzene sulfonate 2.9% Tallow alcohol-tetradecane-ethylene glycol ether (14 mols EO)

3.5% Sodium soap 43.8% Sodium tripolyphosphate 7.5% Sodium silicate 1.9% Magnesium silicate 1.2% Carboxymethyl cellulose 0.2% EDTA 21.2% Sodium sulfate 0 or 0.3% compound (102) and Water to 100%.

Using a liquor ratio of 20:1, washing is conducted with this washing composition for 15 minutes at 40° C. The washed swatches are then rinsed with cold running tap water for 30 seconds at 40° C., spun and dried in the dark.

Each washed swatch is then divided into two parts, an O-part which is stored without exposure to light, and an E-part which is exposed to light in an Atlas Weather-O-Meter instrument, under the following conditions:

lamp energy: 5.0 kW
dry bulb: 29.50° C.
wet bulb: 20.6° C.
wet bulb depression: 9.4° C. (corresponding to relative humidity of 40%)
ambient air: 31.4° C.
lamp-to-fabric distance: so that irradiance on fabric surface is 0.36 W/m$^2$
time: 45 hours.

Evaluation of light fastness: The calorimetric values $L_0$, $a_0$ and $b_0$ of the unexposed O-swatches and the $L_e$, $a_e$ and $b_e$ values of the exposed E-swatches are measured using a Spectraflash SF 500 spectrophotometer having a UV cutting filter up to 460 nm. The colour difference $\Delta E$ between the swatch exposed to light and the corresponding unexposed swatch of the same dyeing, is calculated according to the formula:

$$\Delta E = [(L_e - L_0)^2 + (a_e - a_0)^2 + (b_e - b_0)^2]^{1/2}$$

The difference $d(\Delta E)$ between the $\Delta E$ values, with and without the test compound (102), is a measure of the influence of the test compound on the lightfastness of the given dyeing.

The results obtained are set out in the following Table 2.

| Dyeing conditions | $\Delta E$ without (102) | $\Delta E$ with (102) | $d(\Delta E)$ |
|---|---|---|---|
| 0.125% Cibacron Red FN-3G | 12.9 | 12.1 | 0.8 |
| 0.050% Cibacron Red FN-3G | 12.1 | 10.7 | 1.4 |
| 0.125% Cibacron Yellow F-4G | 8.3 | 7.5 | 0.8 |
| 0.125% Cibacron Yellow F-3R | 3.1 | 2.5 | 0.6 |
| 0.125% Cibacron Orange F-R | 18.7 | 17.3 | 1.4 |
| 0.125% Cibacron Red F-B | 7.6 | 6.6 | 1.0 |
| 0.500% Cibacron Navy F-R | 10.5 | 9.8 | 0.7 |
| 0.500% Cibacron Black F-2B | 11.8 | 11.1 | 0.7 |

These results show that compound (102) improves the lightfastness of the test dyed goods. The improvement is visually clearly perceivable. Its importance depends on the dyestuff.

We claim:

1. A compound having the formula:

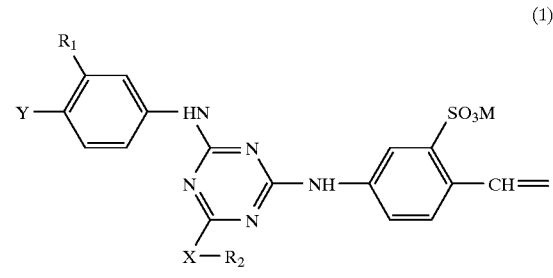

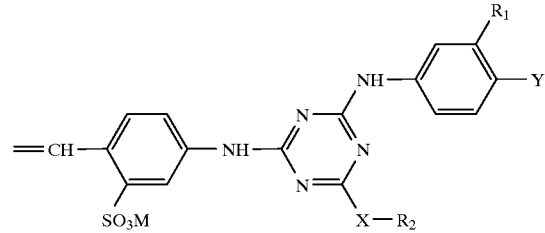

in which M is hydrogen, an alkali metal atom, ammonium or a cation formed from an amine; $R_1$ is hydrogen or hydroxy; $R_2$ is $C_1$–$C_4$alkyl or phenyl; Y is —C(=O)—NR$_3$R$_4$ in which $R_3$ and $R_4$, independently, are hydrogen or $C_1$–$C_4$alkyl, —SO$_2$—NR$_3$R$_4$ in which $R_3$ and $R_4$ have their previous significance, —C(=O)—R$_2$ in which R$_2$ has its previous significance or —C(=O)—OM in which M has its previous significance; and X is NH or O, or X—R$_2$ denotes a morpholino group; provided that those compounds are excluded in which:

a) Y is —C(=O)—OM in which M has its previous significance; X is NH; and R$_2$ is n-butyl or phenyl;
b) R$_1$ is hydrogen; Y is —C(=O)—CH$_3$ or —C(=O)—OM in which M has its previous significance; and X—R$_2$ denotes a morpholino group; or
c) R$_1$ is hydrogen; Y is —C(=O)—OM in which M has its previous significance; X is NH or O; and R$_2$ is methyl.

2. A compound according to claim 1 in which R$_1$ is hydrogen.

3. A compound according to claim 1 in which X is NH.

4. A compound according to claim 1 in which R$_2$ is methyl.

5. A compound according to claim 1 in which Y is —C(=O)—NR$_3$R$_4$ in which R$_3$ and R$_4$, independently, are hydrogen or C$_1$–C$_4$alkyl.

6. A compound according to claim 5 in which Y is —C(=O)—NHCH$_3$.

7. A compound according to claim 1 in which M is a cation formed from an alkali metal.

8. A compound according to claim 7 in which M is sodium.

9. A process for the production of a compound of formula (1) as defined in claim 1 comprising reacting cyanuric chloride, successively, in any desired sequence, with each of an aminostilbene-sulfonic acid, an amino compound capable of introducing a group

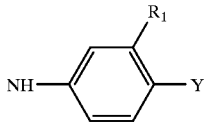

in which R$_1$ and Y are each as defined in claim 1, and a compound capable of introducing a group X—R$_2$, in which X and R$_2$ are each as defined in claim 1.

10. A detergent composition comprising:

i) 5–90% of an anionic surfactant and/or a nonionic surfactant;
ii) 5–70% of a builder;
iii) 0–30% of a peroxide;
iv) 0–10% of a peroxide activator and/or 0–1% of a bleaching catalyst and/or 0.001–0.05% of a photobleaching agent;
v) 0.005–2% of at least one compound of formula (1), as defined in claim 1; and
vi) 0.005–10% of one or more auxiliaries, each by weight, based on the total weight of the detergent.

11. Textile detergent or softener colour care composition comprising a compound of formula (1) as defined in claim 1.

12. Textile detergent or softener colour care composition comprising a non-fluorescent compound of formula (1) as defined in claim 1.

13. A detergent composition according to claim 10 comprising:

i) 5–70% of an anionic surfactant and/or a nonionic surfactant;
ii) 5–40% of a builder;
iii) 1–12% of a peroxide;
iv) 1–6% of a peroxide activator and/or 0.1–0.3% of a bleaching catalyst;
v) 0.01–1% of at least one compound of formula (1); and
vi) 0.1–5% of one or more auxiliaries, each by weight, based on the total weight of the detergent.

* * * * *